US010288589B2

(12) United States Patent
Kudo et al.

(10) Patent No.: US 10,288,589 B2
(45) Date of Patent: May 14, 2019

(54) MASS SPECTROMETRY METHOD AND MASS SPECTROMETER

(71) Applicant: SHIMADZU CORPORATION, Kyoto-shi, Kyoto (JP)

(72) Inventors: Yukihiko Kudo, Kyoto (JP); Kenichi Obayashi, Kyoto (JP); Syuichi Kawana, Kyoto (JP)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 232 days.

(21) Appl. No.: 15/123,270

(22) PCT Filed: Mar. 5, 2014

(86) PCT No.: PCT/JP2014/055601
§ 371 (c)(1),
(2) Date: Sep. 2, 2016

(87) PCT Pub. No.: WO2015/132901
PCT Pub. Date: Sep. 11, 2015

(65) Prior Publication Data
US 2017/0067864 A1    Mar. 9, 2017

(51) Int. Cl.
*G06F 11/30* (2006.01)
*G01N 30/86* (2006.01)
(Continued)

(52) U.S. Cl.
CPC ..... *G01N 30/8631* (2013.01); *G01N 30/7266* (2013.01); *H01J 49/0036* (2013.01); *G01N 30/7233* (2013.01); *H01J 49/0045* (2013.01)

(58) Field of Classification Search
CPC ............................................... G01N 30/8631
See application file for complete search history.

(56) References Cited

U.S. PATENT DOCUMENTS

| 8,653,447 B2 | 2/2014 | Mukaibatake |
| 2013/0284919 A1 | 10/2013 | Mukaibatake |
| 2013/0297230 A1 | 11/2013 | Kawase |

FOREIGN PATENT DOCUMENTS

| CN | 103282768 A | 9/2013 |
| CN | 103389345 A | 11/2013 |

(Continued)

OTHER PUBLICATIONS

Written Opinion for PCT/JP2014/055601 dated Apr. 1, 2014. [PCT/ISA/237].

(Continued)

*Primary Examiner* — Phuong Huynh
(74) *Attorney, Agent, or Firm* — Sughrue Mion, PLLC

(57) ABSTRACT

In a mass spectrometry method for performing a qualitative and/or quantitative determination of an analyte compound contained in a sample, using a mass chromatogram acquired for one or a plurality of ions selected as a reference ion from the ions produced from the analyte compound, the present method includes the steps of: setting one or a plurality of reference-ion candidates for each of the one or a plurality of reference ions; acquiring a mass chromatogram of the sample for each of the set reference-ion candidates; calculating a shape similarity between a peak appearing at a predetermined position on the mass chromatogram and a preset model peak; and designating, as the reference ion, a reference-ion candidate corresponding to a peak having the shape similarity equal to or higher than a predetermined value.

12 Claims, 10 Drawing Sheets

(51) Int. Cl.
*H01J 49/00* (2006.01)
*G01N 30/72* (2006.01)

(56) References Cited

FOREIGN PATENT DOCUMENTS

| | | |
|---|---|---|
| EP | 2 660 589 A1 | 11/2013 |
| JP | H10-318983 A | 12/1998 |
| JP | 2010-054406 A | 3/2010 |
| JP | 2011-242255 A | 12/2011 |
| JP | 2012-104389 A | 5/2012 |
| JP | 2012-132799 A | 7/2012 |
| JP | 2013-15485 A | 1/2013 |
| JP | 2013-195099 A | 9/2013 |
| JP | 2013-234859 A | 11/2013 |
| WO | 2005/114930 A2 | 12/2005 |
| WO | WO 2005114930 * | 12/2005 |
| WO | 2012/080443 A1 | 6/2012 |
| WO | 2012/090308 A1 | 7/2012 |

OTHER PUBLICATIONS

Communication dated Aug. 1, 2017, from Japanese Patent Office in counterpart application No. 2016-505997.
International Search Report for PCT/JP2014/055601 dated Apr. 1, 2014 [PCT/ISA/210].
Communication dated Jan. 23, 2017, issued from the European Patent Office in corresponding European Application No. 14884793.2.

* cited by examiner

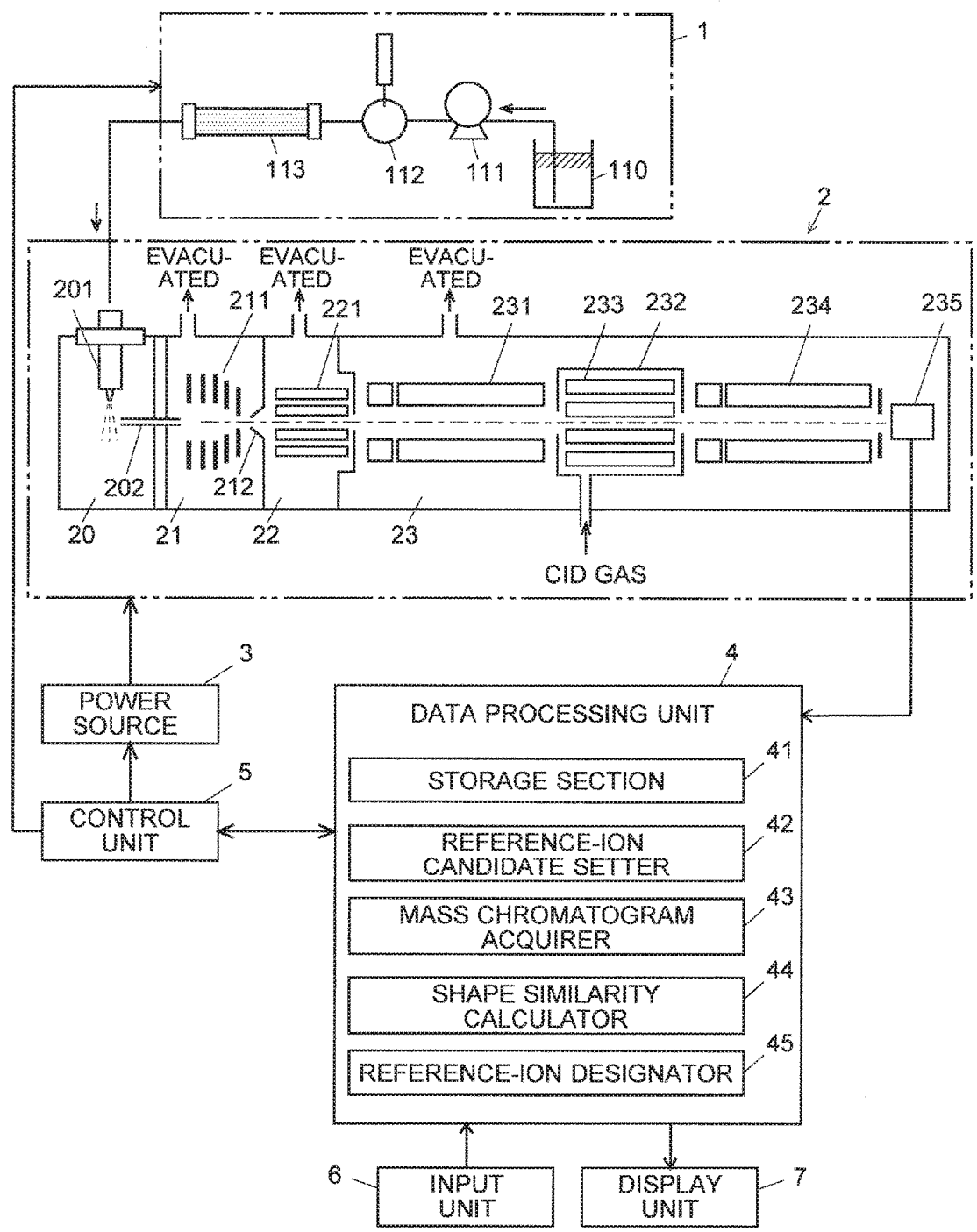

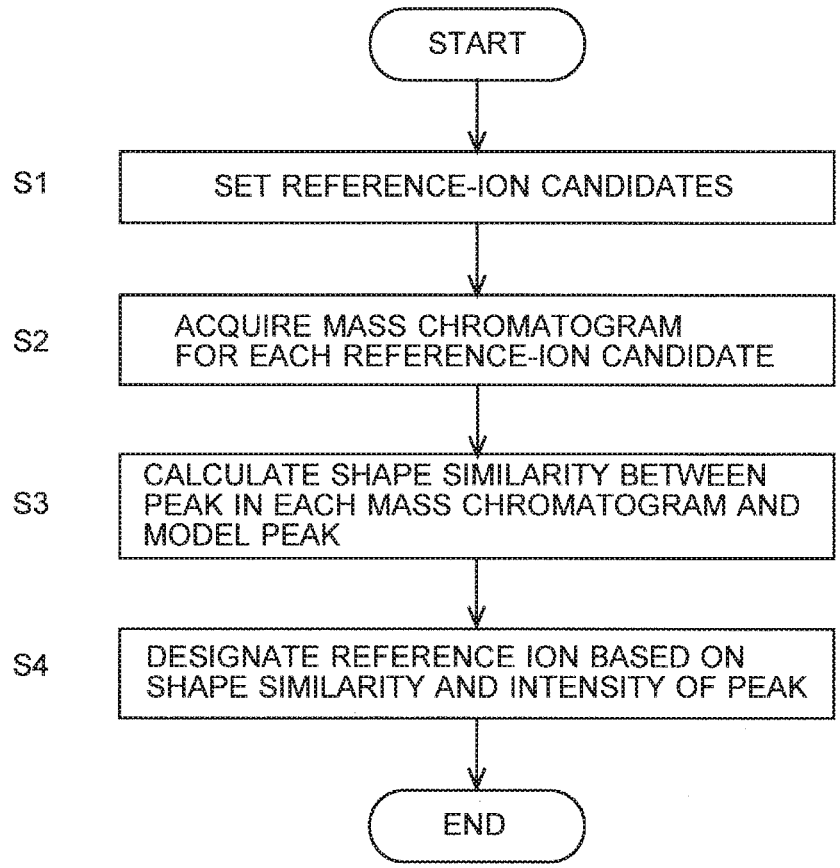

| COM-POUND NAME | RETENTION TIME (min) | TARGET ION CANDIDATE ||| QUALIFIER ION CANDIDATE ||| INTEN-SITY RATIO |
|---|---|---|---|---|---|---|---|---|
| | | ION NAME | m/z | INTEN-SITY | ION NAME | m/z | INTEN-SITY | |
| A | ta | a | 150.00 | 100 | b | 135.00 | 75 | 1.33 |
| A | ta | a | 150.00 | 100 | c | 120.00 | 60 | 1.67 |
| A | ta | a | 150.00 | 100 | d | 100.00 | 20 | 5.00 |
| A | ta | b | 135.00 | 75 | c | 120.00 | 60 | 1.25 |
| A | ta | b | 135.00 | 75 | d | 100.00 | 20 | 3.75 |
| A | ta | c | 120.00 | 60 | d | 100.00 | 20 | 3.00 |

| COM-POUND NAME | RETENTION TIME (min) | REFERENCE MRM TRANSITION CANDIDATE | | | | |
|---|---|---|---|---|---|---|
| | | TRANSITION NAME | PRECURSOR ION (m/z) | PRODUCT ION (m/z) | CE (V) | INTEN-SITY |
| B | tb | a | AAA | aaa | 5.00 | 100 |
| B | tb | b | BBB | bbb | 4.50 | 75 |
| B | tb | c | CCC | ccc | 3.60 | 60 |
| B | tb | d | DDD | ddd | 4.00 | 20 |

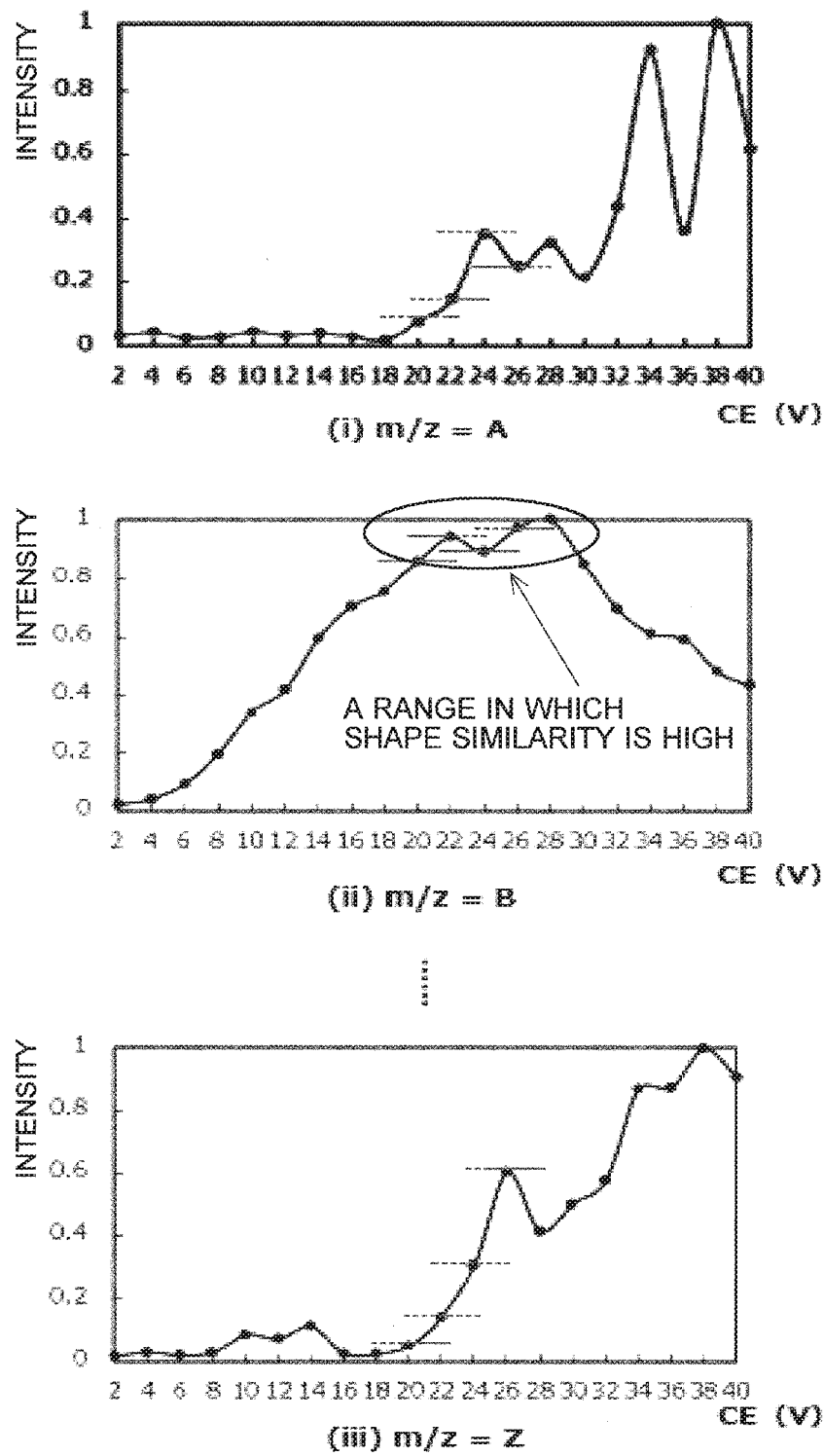

MASS SPECTROMETRY METHOD AND MASS SPECTROMETER

CROSS REFERENCE TO RELATED APPLICATIONS

This application is a National Stage of International Application No. PCT/JP2014/055601, filed on Mar. 5, 2014, the contents of all of which are incorporated herein by reference in their entirety.

TECHNICAL FIELD

The present invention relates to a mass spectrometry method and system for performing a qualitative and/or quantitative determination of a compound to be analyzed (which is hereinafter called the "analyte compound") contained in a sample, using a mass chromatogram acquired for one or a plurality of ions selected as a reference ion (such as the target ion or qualifier ion) from the ions produced from the analyte compound.

BACKGROUND ART

For a qualitative or quantitative analysis of the components contained in a sample, a chromatograph mass spectrometer is widely used, which is an apparatus including a chromatograph, such as a gas chromatograph (GC) or liquid chromatograph (LC), combined with a mass spectrometer, such as a quadrupole mass analyzer.

In a chromatograph mass spectrometer, a plurality of components in a sample temporally separated by the chromatograph are sequentially introduced into the mass spectrometer, in which a qualitative or quantitative analysis of those components is performed.

To perform a qualitative or quantitative analysis of a sample using a chromatograph mass spectrometer, specific ions which characterize the analyte compound are previously set as the target ion and qualifier ion. For each of a variety of compounds, one or more combinations of ions are previously designated as the target ion and qualifier ion, and stored in a database, based on the result of a mass spectrometry performed for a standard sample of the compound concerned. An analysis operator refers to this database and sets the target ion and qualifier ion. The compound is identified (qualitatively determined) using the intensity ratio (or area ratio) between the peak in a mass chromatogram of the target ion and the peak in a mass chromatogram of the qualifier ion obtained by a chromatographic mass spectrometry of the sample, while the quantity of the compound is determined from the intensity (or area) of the peak in the mass chromatogram of the target ion (for example, see Patent Literature 1 or 2).

CITATION LIST

Patent Literature

Patent Literature 1: JP 2011-242255 A
Patent Literature 2: JP 2012-132799 A
Patent Literature 3: JP 2013-15485 A
Patent Literature 4: JP 2012-104389 A

SUMMARY OF INVENTION

Technical Problem

The target ions and qualifier ions stored in the database for various compounds are determined based on the result of the mass spectrometry of a standard sample which contains no other components than the compound in question. However, real samples contain a plurality of components. A foreign component may be eluted with almost the same retention time as the analyte compound, and an ion derived from that foreign component may have almost the same mass-to-charge ratio as the analyte compound. In such a case, the peak of the ion derived from the foreign component overlaps the peak of the ion derived from the analyte compound on the mass chromatogram, with the result that an incorrect value which additionally includes the content of the foreign component is obtained as the quantitative value of the analyte compound.

Therefore, analysis operators perform the task of examining the peak shape or other features of the mass chromatogram acquired for the target ion or qualifier ion of the sample to determine whether or not a peak of an ion generated from a foreign component is overlapped, and selecting different ions as the target ion and qualifier ion if an overlapping peak is found. Such a task consumes much time as well as imposes a heavy load on the analysis operator.

Such a problem is not limited to the previously mentioned case: A similar problem occurs in the case of setting a target MRM transition (a combination of the precursor ion and product ion which corresponds to the target ion) and a qualifier MRM transition (which corresponds to the qualifier ion) in a multiple reaction monitoring (MRM) analysis using an MS/MS system.

In the following descriptions, the target ion, qualifier ion, target MRM transition and qualifier MRM transition are appropriately called the "reference ion".

The problem to be solved by the present invention is to provide a method and system for chromatographic mass spectrometry with which a reference ion free from the influence of foreign components can be easily select for a qualitative and/or quantitative determination of an analyte compound contained in a sample.

Solution to Problem

The present invention developed for solving the previously described problem is a mass spectrometry method for performing a qualitative and/or quantitative determination of an analyte compound contained in a sample, using a mass chromatogram acquired for one or a plurality of ions selected as a reference ion from the ions produced from the analyte compound, the method including the steps of:

a) setting one or a plurality of reference-ion candidates for each of the one or a plurality of reference ions;

b) acquiring a mass chromatogram of the sample for each of the set reference-ion candidates;

c) calculating a shape similarity between a peak appearing at a predetermined position on the mass chromatogram and a model peak represented by a previously defined function; and d) designating, as the reference ion, a reference-ion candidate corresponding to a peak having the shape similarity equal to or higher than a predetermined value.

Examples of the reference ion include the previously mentioned target ion or qualifier ion, as well as the target MRM transition or qualifier MRM transition, which is the combination of a precursor ion and a product ion. The "predetermined position on the mass chromatogram" is the position corresponding to the retention time of the analyte compound.

In the mass spectrometry method according to the present invention, the shape similarity between the peak which appears at a predetermined position on the mass chromatogram and the preset model peak is calculated. An ion corresponding to a peak having a shape similarity equal to or higher than a predetermined value is designated as the reference ion. If the peak located on the mass chromatogram is a peak which is purely formed by a single kind of ion, its shape should be highly similar to the shape of the model peak which is represented, for example, by a Gaussian function. By comparison, if a peak derived from a foreign component is overlapped on it, the peak will be deformed and its shape similarity to the model peak will be low. Therefore, by selecting, as the reference ion, an ion which forms a peak having a shape similarity equal to or higher than a predetermined value, a reference ion free from the influence of foreign components can be selected. With the chromatographic mass spectrometry method according to the present invention, analysis operators can easily select a reference ion free from the influence of foreign components without performing the task of examining the peak shape on the mass chromatogram by themselves.

For example, a peak represented by a Gaussian function or similar function, or a peak obtained by actually analyzing a standard sample of the analyte compound can be used as the model peak. The shape similarity can be calculated, for example, by the Pearson correlation method.

The second aspect of the present invention is a mass spectrometer for performing a qualitative and/or quantitative determination of an analyte compound contained in a sample, using a mass chromatogram acquired for one or a plurality of ions selected as a reference ion from the ions produced from the analyte compound, the mass spectrometer including:

a) a storage section for holding model-peak information concerning the peak shape of a model peak represented by a previously defined function;

b) a reference-ion candidate setter for setting one or a plurality of reference-ion candidates for each of the one or a plurality of ions according to a direction entered by a user;

c) a mass chromatogram acquirer for acquiring a mass chromatogram of the sample for each of the set reference-ion candidates;

d) a shape similarity calculator for calculating a shape similarity between a peak appearing at a predetermined position on the mass chromatogram and the model peak based on the model-peak information; and e) a reference-ion designator for designating, as the reference ion, a reference-ion candidate corresponding to a peak having the shape similarity equal to or higher than a predetermined value.

The third aspect of the present invention developed for solving the previously described problem is a mass spectrometry method for performing a qualitative and/or quantitative determination of an analyte compound contained in a sample, using mass chromatograms acquired for two kinds of ions designated as a target ion and a qualifier ion from the ions produced from the analyte compound, the method including the steps of:

a) setting one or a plurality of combinations of target-ion candidates and qualifier-ion candidates;

b) acquiring a mass chromatogram of the sample for each of the set combinations of the target-ion candidates and the qualifier-ion candidates;

c) calculating the value of an area ratio or intensity ratio between a peak appearing at a predetermined position on the mass chromatogram of the target-ion candidate and a peak appearing at the predetermined position on the mass chromatogram of the qualifier-ion candidate; and d) designating, as a combination of the target ion and the qualifier ion, a combination of the target-ion candidate and the qualifier-ion candidate if the value of the area ratio or intensity ratio calculated for this combination is within a preset range.

As already noted, one or more combinations of target ions and qualifier ions are set for each of a variety of compounds based on the result of a mass spectrometry performed on a standard sample of each compound. Those combinations are previously stored in a database, along with the values of the area ratio and/or intensity ratio of the peaks on the mass chromatograms acquired for those combinations. Accordingly, the aforementioned range can be previously set with reference to the information in the database.

The target ion and qualifier ion include a target MRM transition and qualifier MRM transition.

In the third aspect of the present invention, the target ion and qualifier ion are not selected based on the peak shape, but on the area ratio or intensity ratio between the peaks on mass chromatograms acquired for two kinds of ions. If a peak of an ion derived from a foreign component is overlapped on the peak in the mass chromatogram of the target ion or qualifier ion, the area or intensity of the peak corresponding to the ion derived from that foreign component is added to the area or intensity of the peak of interest, so that the value of the area ratio or intensity ratio between the peaks of the target ion and qualifier ion deviates from the value range stored in the database. Therefore, it is possible to select a target ion and qualifier ion free from the influence of foreign components by using a combination of the ions which satisfy the condition that the value of the area ratio or intensity ratio between the peaks in the mass chromatograms should be within a specific range defined with reference to the database.

The fourth aspect of the present invention developed for solving the previously described problem is a mass spectrometer for performing a qualitative and/or quantitative determination of an analyte compound contained in a sample, using mass chromatograms acquired for two kinds of ions designated as a target ion and a qualifier ion from the ions produced from the analyte compound, the mass spectrometer including:

a) a storage section for holding ion-combination information concerning an area ratio and/or intensity ratio between the peaks on the mass chromatograms for each of one or a plurality of combinations of target-ion candidates and qualifier-ion candidates corresponding to the analyte compound;

b) an ion-candidate combination setter for setting one or a plurality of combinations of target-ion candidates and qualifier-ion candidates according to a direction entered by a user;

c) a mass chromatogram acquirer for acquiring a mass chromatogram of the sample for each of the set combinations of the target-ion candidates and the qualifier-ion candidates;

d) a peak ratio calculator for calculating the value of the area ratio or intensity ratio between a peak appearing at a predetermined position on the mass chromatogram of the target-ion candidate and a peak appearing at the predetermined position on the mass chromatogram of the qualifier-ion candidate; and e) an ion-combination designator for designating, as the target ion and the qualifier ion, a combination selected from the combinations of the target-ion candidates and the qualifier-ion candidates based on the ion-combination information.

Advantageous Effects of the Invention

With the mass spectrometry method and system according to the present invention, a reference ion free from the influence of foreign components can be easily selected for a qualitative and/or quantitative determination of an analyte compound in a sample by mass spectrometry.

BRIEF DESCRIPTION OF DRAWINGS

FIG. 1 is a configuration diagram showing the main components of a mass spectrometer in the first embodiment.

FIG. 2 is an example of the compound information used in the first embodiment.

FIG. 3 is a flowchart in the mass spectrometry method in the first embodiment.

FIG. 16 is a diagram illustrating an example of the range where the shape similarity of the product-ion intensity graph is high in the fourth embodiment.

DESCRIPTION OF EMBODIMENTS

Figure 4A:
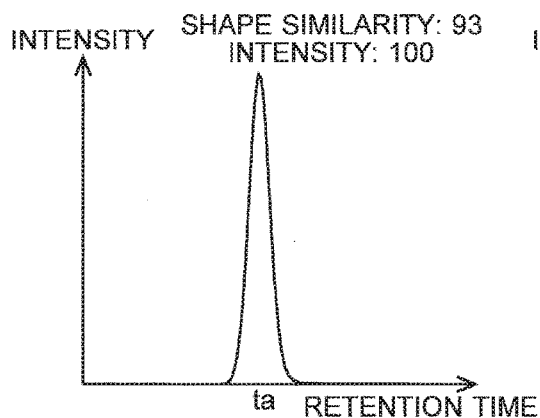
FIGS. 4A-4D are diagrams illustrating the peak shape and peak intensity in the first embodiment.

Embodiments of the mass spectrometer and mass spectrometry method according to the present invention are hereinafter described with reference to the drawings.

First Embodiment

FIG. 1 shows the configuration of the main components of a liquid chromatogram mass spectrometer in the first embodiment.

In the liquid chromatograph mass spectrometer of the present embodiment, the liquid chromatograph unit 1 includes a mobile phase container 110 holding a mobile phase, a pump 111 for drawing and supplying the mobile phase at a fixed flow rate, an injector 112 for injecting a predetermined amount of prepared sample into the mobile phase, and a column 113 for temporally separating the various compounds contained in the sample. The pump 111 draws the mobile phase from the mobile phase container 110 and supplies it at a fixed flow rate to the column 113. When a fixed amount of sample liquid is introduced from the injector 112 into the mobile phase, the sample is carried by the flow of the mobile phase into the column 113. While passing through the column 113, the various compounds in the sample are temporally separated and eluted from the exit port of the column 113, to be introduced into the mass spectrometer 2.

The mass spectrometer 2 has the configuration of a multistage differential pumping system including an ionization chamber 20 maintained at substantially atmospheric pressure and an analysis chamber 23 evacuated to a high degree of vacuum by a vacuum pump (not shown), between which first and second intermediate vacuum chambers 21 and 22 are provided having their degrees of vacuum increased in a stepwise manner. An electrospray ionization (ESI) probe 201 for spraying a sample solution while imparting electric charges is provided within the ionization chamber 20. The ionization chamber 20 and the first intermediate chamber 21 in the next stage communicate with each other through a thin heated capillary 202. The first intermediate vacuum chamber 21 is separated from the second intermediate vacuum chamber 22 by a skimmer 212 having a small hole at its apex. Ion guides 211 and 221 for transporting ions while converging them are placed within the first and second intermediate vacuum chambers 21 and 22, respectively. The analysis chamber 23 contains a front quadrupole mass filter (Q1) 231 which separates ions according to their mass-to-charge ratios and a rear quadrupole mass filter (Q3) 234 which also separates ions according to their mass-to-charge ratios, with a collision cell 232 containing a multipole ion guide 233 placed between the two filters, as well as an ion detector 235 placed after the rear quadrupole mass filter 234. A power source 3 applies predetermined voltages to the ESI probe 201, ion guides 211, 221 and 233, quadrupole mass filters 231 and 234, as well as other elements. In each of the quadrupole mass filters 231 and 234, pre-rod electrodes for correcting the disturbance of the electric field at the inlet end are provided before the main rod electrodes. A voltage which is different from those applied to the main rod electrodes can be applied to the pre-rod electrodes.

The mass spectrometer 2 is configured to be capable of an MS/MS analysis. However, the analysis performed in the first embodiment is an MS analysis. More specifically, only the front quadrupole mass filter 231 is used as the mass separator, with no CID gas supplied into the collision cell 232, while the multipole ion guide 233 and the rear quadrupole mass filter 234 are supplied with voltages which allow the passage of all ions that have been mass-separated by the front quadrupole mass filter 231. Instead of the LC/MS/MS system of the present embodiment, an LC/MS system in which the LC is coupled with a mass spectrometer specialized for MS analysis may also be used.

In the mass spectrometer 2, when an eluate from the column 113 reaches the electrospray ionization probe 201, the eluate is sprayed from the probe 201 while receiving electric charges from the tip of it. The charged droplets formed in this spraying process are gradually divided into smaller sizes by an electrostatic force due to the imparted electric charges. During this process, the solvent turns into vapor, releasing ions originating from compounds. The ions produced in this manner are sent through the heated capillary 202 into the first intermediate vacuum chamber 21, where the ions are converged by the ion guide 211, to be sent through the small hole at the apex of the skimmer 212 into the second intermediate vacuum chamber 22. The compound-originated ions are converged by the ion guide 221 and sent into the analysis chamber 23, where the ions are introduced into the space extending along the longitudinal axis of the front quadrupole mass filter 231. It should be noted that the ionization method is not limited to the electrospray ionization. Other methods may also be used, such as the atmospheric pressure chemical ionization or atmospheric pressure photoionization.

A predetermined form of voltage (composed of a radio-frequency voltage and a direct-current voltage superposed on each other) is applied from the power source 3 to each of the rod electrodes of the front quadrupole mass filter 231 in which the MS analysis is performed. Among the various ions sent into the front quadrupole mass filter 231, only an ion having a specific mass-to-charge ratio corresponding to the voltage applied to the rod electrodes of the quadrupole mass filter 231 is allowed to pass through this filter. This ion subsequently passes through the collision cell 232 and the rear quadrupole mass filter 234, to be eventually detected by the ion detector 235. One example of the ion detector 235 is a pulse-counting detector, which generates pulse signals whose number corresponds to the number of incident ions. Those signals are sent to a data processing unit 4 as detection signals.

The data processing unit 4 has a storage section 41 as well as a reference-ion candidate setter 42, mass chromatogram acquirer 43, shape similarity calculator 44 and reference-ion designator 45 as its functional blocks. The storage section 41 holds model-peak function information (e.g. a Gaussian function, EMG function, Bigaussian function or skew normal function) as well as compound information which includes: the retention time (or retention index) related to the analyte compound; and the mass-to-charge ratio and peak intensity of the reference-ion candidate. FIG. 2 shows one example of the compound information for compound "A" stored in the storage section 41. The compound information is prepared beforehand based on the result of a mass spectrometry performed for a standard sample of the compound concerned.

The data processing unit 4 is configured to appropriately send and receive signals to and from a control unit 5, which controls the operations of the pump 111 and the injector 112 in the liquid chromatograph unit 1, the power source 3 and the CID gas supplier (not shown) in the mass spectrometer 2, as well as other sections of the system. The data processing unit 4 is actually a personal computer, which functions as the data processing unit 4 when a dedicated data processing software program previously installed on the same computer is executed. Additionally, an input unit 6 and display unit 7 are connected to the data processing unit 4.

The mass spectrometry method in the first embodiment is hereinafter described with reference to the flowchart of FIG. 3.

An analysis operator refers to the compound information of compound "A" stored in the storage section 41 and enters a plurality of reference-ion candidates for compound "A". The reference-ion candidate setter 42 sets those candidates as the reference-ion candidates (Step S1). Alternatively, the reference-ion candidate setter 42 may read the compound information from the storage section 41 and automatically set the reference-ion candidates based on that information.

Subsequently, the mass chromatogram acquirer 43 sends a predetermined signal to the control unit 5 to operate the liquid chromatograph unit 1 and the mass spectrometer 2 so as to acquire a mass chromatogram for each of the reference-ion candidates (Step S2). Specifically, a sample which contains the analyte compound (i.e. compound "A") is injected through the injector 112 of the liquid chromatograph unit into the flow of a predetermined kind of mobile phase, which carries the sample through the column 113 into the mass spectrometer 2. In the mass spectrometer 2, the quadrupole mass filter 231, to which a predetermined form of voltage is applied from the power source 3, selectively allows the ion designated as the reference-ion candidate to pass through it and be detected by the ion detector 235. Based on the detection signals from the ion detector 235, the mass chromatogram acquirer 43 creates a mass chromatogram for the reference-ion candidate and saves it in the storage section 41. It also displays the mass chromatogram on the screen of the display unit 7.

After the mass chromatograms have been acquired for all reference-ion candidates, the shape similarity calculator 44 extracts the peak corresponding to the retention time (ta) of compound "A" in each mass chromatogram, and calculates the shape similarity between the extracted peak and the model peak (Step S3). As in the present embodiment, when there are a plurality of model-peak functions, the shape similarity calculator 44 prompts the analysis operator to select the function to be used, and calculates the shape similarity using the selected function. Various methods are available for the calculation of the shape similarity, such as the method using the Pearson correlation coefficient, cosine similarity, Spearman's rank correlation coefficient, Kendall rank correlation coefficient, Jaccard coefficient, Dice's coefficient, or Simpson coefficient. It is also possible to calculate the similarity by determining the degree of difference from the model peak using a distance between two vectors (e.g. Euclidean distance, Manhattan distance, Chebyshev distance or Minkowski distance).

FIGS. 4A-4D show the peaks in the mass chromatogram acquired for reference-ion candidates "a" through "d", respectively, along with the shape similarity and intensity value of each peak. The reference-ion designator 45 initially selects reference-ion candidates "a", "c" and "d" whose peak-shape similarities are equal to or higher than a predetermined value (in the present embodiment, 80). Subsequently, it selects two reference-ion candidates "a" and "c" in descending order of the intensity value from the three reference-ion candidates, and designates them as the target ion and the qualifier ion (Step S4). In the case where only the target ion needs to be designated as the reference ion, the reference-ion candidate "a" having the highest intensity value is solely selected and designated as the target ion.

Figure 4B:
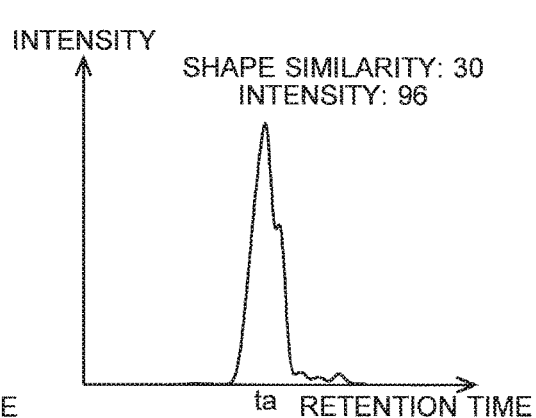
Figure 4C:
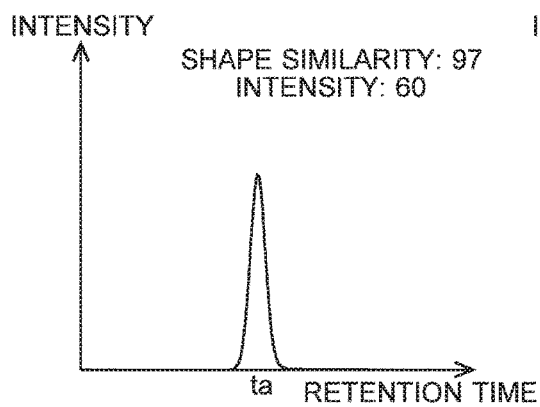
Figure 4D:
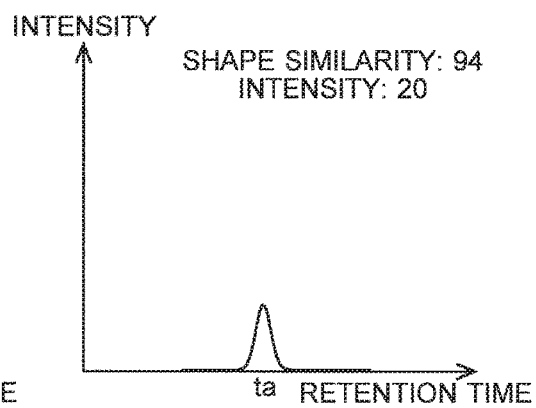

As shown in FIG. 4B, the peak of the reference-ion candidate "b" has another peak which has appeared in the base portion of the peak, which means that a peak of a foreign component is overlapped on the peak of the target compound. Calculating the shape similarity between such a peak and the model peak yields a low value. Accordingly, it is possible to select a reference ion free from the influence of foreign components by selecting only the reference-ion candidates whose shape similarities are equal to or higher than a predetermined value.

Second Embodiment

Figure 5:
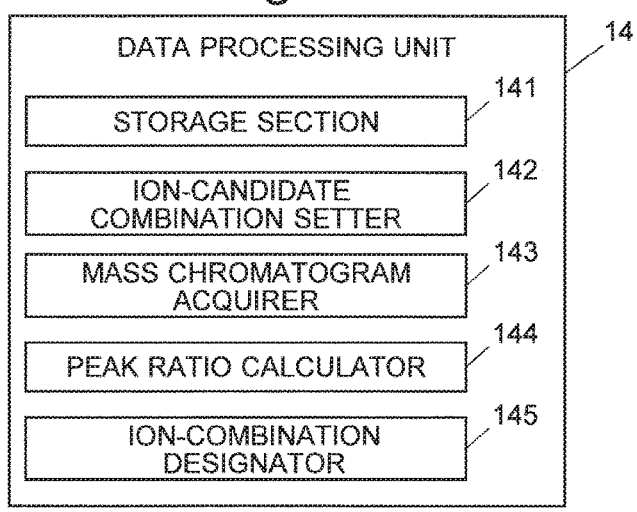
FIG. 5 is a diagram illustrating the configuration of the data processing unit of the mass spectrometer in the second embodiment.

Next, a chromatograph mass spectrometer and mass spectrometry method in the second embodiment are described. The chromatograph mass spectrometer in the present embodiment has the same configuration as the chromatograph mass spectrometer in the first embodiment except for the data processing unit 14. Accordingly, only the configuration of the data processing unit 14 is shown in FIG. 5.

The data processing unit 14 has a storage section 141 as well as an ion-candidate combination setter 142, mass chromatogram acquirer 143, peak ratio calculator 144, and ion-combination designator 145 as its functional blocks. The storage section 141 holds compound information which includes: the retention times (or retention indices) related to various compounds; the mass-to-charge ratios of the target-ion candidate and the qualifier-ion candidate; and the peak intensity ratio (or area ratio) between the two ion candidates (see FIG. 6).

An operation of the liquid chromatograph mass spectrometer in the present embodiment is hereinafter described with reference to the flowchart of FIG. 7.

Initially, the ion-candidate combination setter 142 sets a combination of the target-ion candidate and the qualifier-ion candidate based on an input by an analysis operator or automatically based on the compound information stored in the storage section 141 (Step S11).

Subsequently, the mass chromatogram acquirer 143 sends a predetermined signal to the control unit 5 to operate the liquid chromatograph unit 1 and the mass spectrometer 2 so as to acquire a mass chromatogram for each target-ion candidate as well as for each qualifier-ion candidate (Step S12). The acquired mass chromatograms are saved in the storage section 141 and are also displayed on the screen of the display unit 7.

After the mass chromatograms have been acquired for all ion candidates, the peak ratio calculator 144 calculates the peak intensity ratio (or area ratio) for each combination of the ion candidates (Step S13). From all of the ion-candidate combinations, the ion-combination designator 145 selects the ion-candidate combinations which satisfy the condition that the computed peak intensity ratio falls within a predetermined range (e.g. within ±20%) relative to the intensity ratio in the compound information stored in the storage section 141. Furthermore, from these selected ion-candidate combinations, the ion-combination designator 145 selects the combination having the largest sum of the peak intensity values, and designates this ion-candidate combination as the combination of the target ion and the qualifier ion (Step S14).

As one specific example, the following description deals with the case where the peaks as shown in FIGS. 4A-4D have been respectively obtained for ions "a" through "d" which have been set as the target-ion candidate and/or the qualifier-ion candidate.

Figures 6, 7:
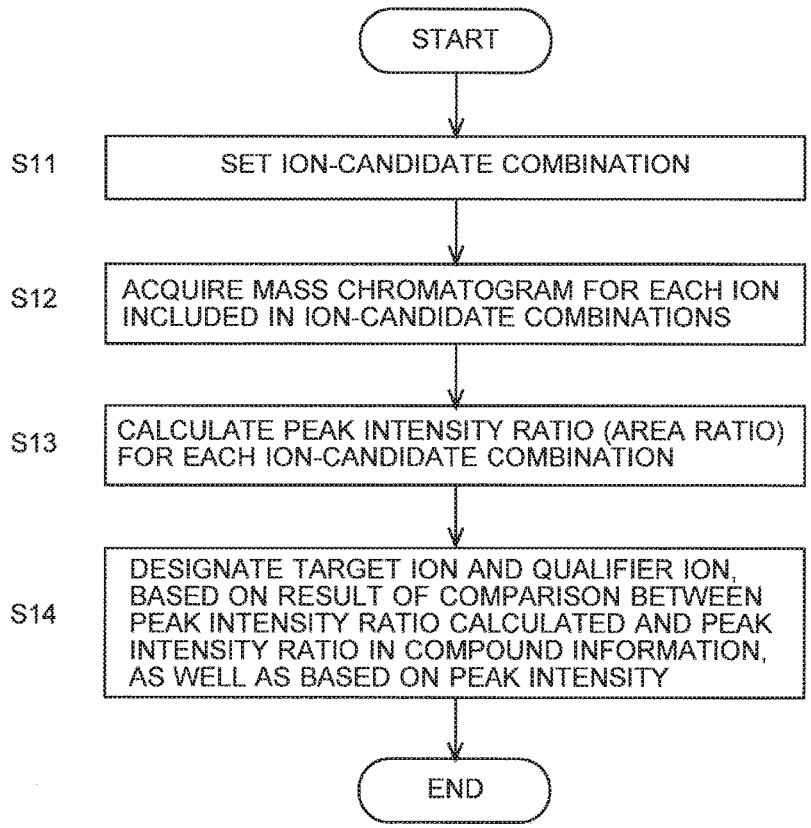
FIG. 6 is an example of the compound information used in the second embodiment.
FIG. 7 is flowchart in the mass spectrometry method in the second embodiment.

As shown in FIG. 6, there are six combinations of ion candidates listed for compound "A" in the compound information. Accordingly, the peak intensity ratio is calculated for each of those combinations. As already noted, the mass chromatogram acquired for ion candidate "b" has a peak of a foreign component overlapped on the peak of compound "A", which means that the peak intensity of compound "A" shown in that mass chromatogram additionally contains the intensity value due to the foreign component. As a result, the peak intensity ratio between any pair of ion candidates including the ion candidate "b" deviates from the value of the peak intensity ratio included in the compound information. Therefore, it is possible to designate a combination of ions free from the influence of foreign components as the target ion and the qualifier ion by selecting an ion-candidate combination which satisfies the condition that the peak intensity ratio between the mass chromatograms respectively acquired for the ion candidates concerned is within a predetermined range relative to the peak intensity ratio included in the compound information.

As opposed to the present embodiment in which the ions having the largest sum of the peak intensity values are designated as the target ion and the qualifier ion, a combination which has the calculated intensity ratio closest to the peak intensity ratio in the compound information may be selected as the combination of the target ion and the qualifier ion.

Third Embodiment

Subsequently, a mass spectrometer and mass spectrometry method in the third embodiment are described.

Figures 8, 9:
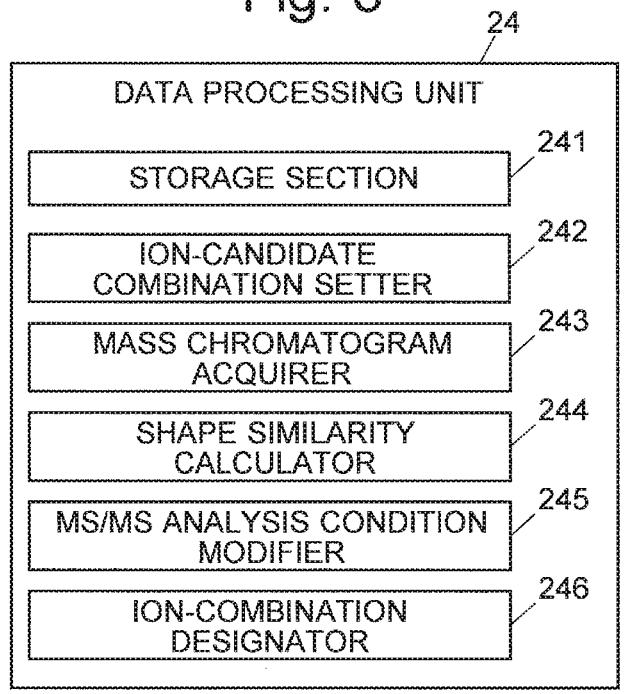
FIG. 8 is a diagram illustrating the configuration of the data processing unit of the mass spectrometer in the third embodiment.
FIG. 9 is an example of the compound information used in the third embodiment.

In the first embodiment, the target ion and the qualifier ion are selected by an MS analysis. By comparison, in the third embodiment, a target MRM transition and qualifier MRM transition are selected by an MS/MS analysis. The configuration of each section of the liquid chromatograph mass spectrometer in the third embodiment is the same as in the first embodiment except for the data processing unit 24. Accordingly, only the configuration of the data processing unit 24 is shown in FIG. 8.

The data processing unit 24 has a storage section 241 as well as an ion-candidate combination setter 242, mass chromatogram acquirer 243, shape similarity calculator 244, MS/MS analysis condition modifier 245, and ion-combination designator 246 as its functional blocks. The storage section 241 holds the model-peak function information described in the first embodiment, as well as compound information which includes: the retention time (or retention index) for the analyte compound; the mass-to-charge ratios of the reference MRM transition candidate (a combination of the precursor ion and the product ion); the value of the collision energy (CE) corresponding to the MRM transition candidate; and the peak intensity. FIG. 9 shows one example of the compound information stored in the storage section 241. The compound information is prepared beforehand, based on the result of a mass spectrometry performed for a standard sample.

Figure 10:
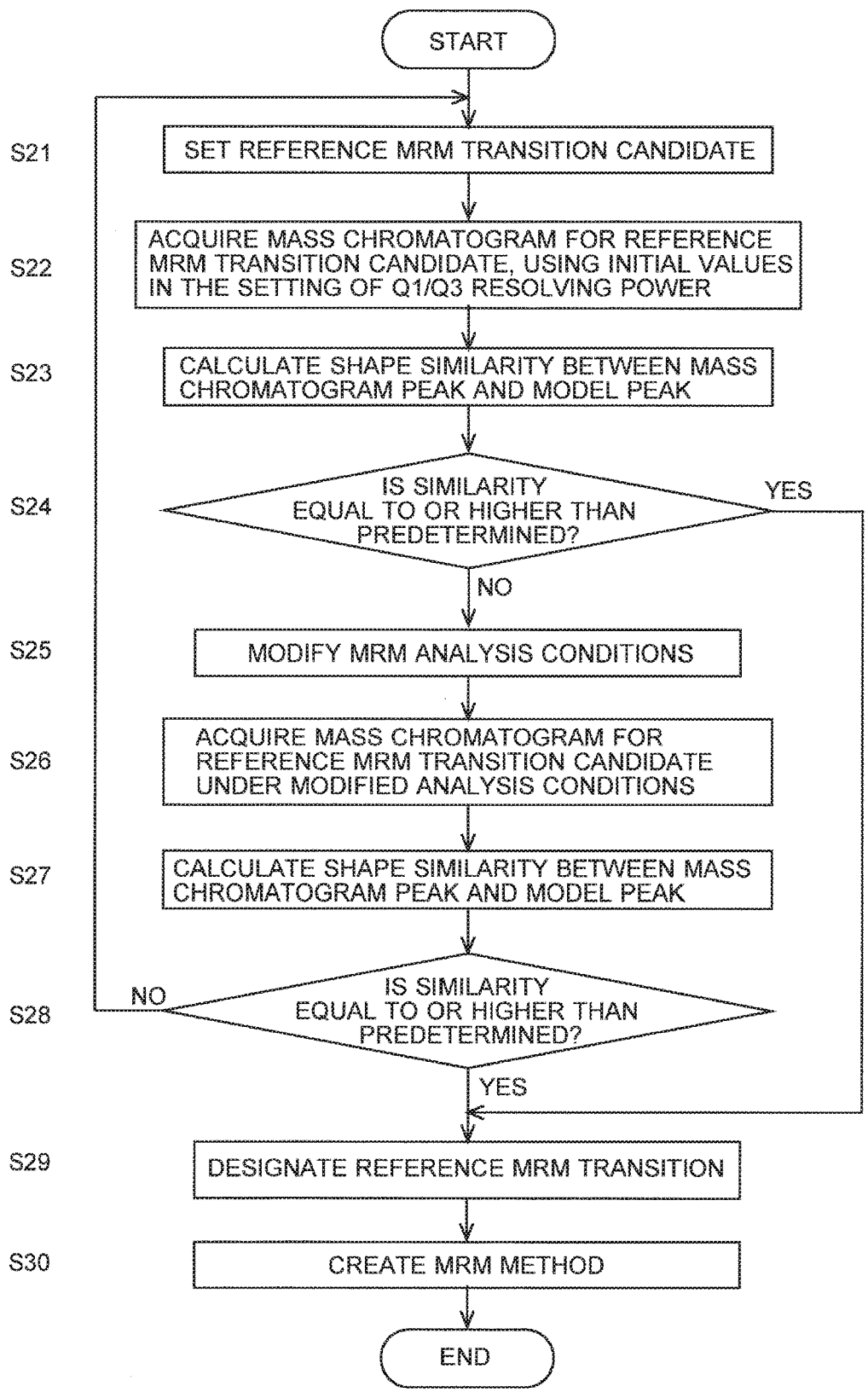
FIG. 10 is a flowchart in the mass spectrometry method in the third embodiment.

The mass spectrometry method in the third embodiment is described with reference to the flowchart of FIG. 10.

Initially, the ion-candidate combination setter 242 reads the reference MRM transition candidate ranked first in the compound information (which is the transition "a" in the present embodiment) and sets it as the reference MRM transition candidate (Step S21).

Subsequently, the mass chromatogram acquirer 243 sends a predetermined signal to the control unit 5 to operate the liquid chromatograph unit 1 and the mass spectrometer 2 so as to acquire a mass chromatogram for the reference MRM transition candidate (Step S22). The operation of each section in this process is as follows:

In the liquid chromatograph unit 1, a sample which contains the analyte compound (i.e. compound "B") is injected through the injector 112 into the flow of a predetermined kind of mobile phase, which carries the sample through the column 113 into the mass spectrometer 2.

In the mass spectrometer 2, a predetermined form of voltage (composed of a radio-frequency voltage and a direct-current voltage superposed on each other) is applied to each of the rod electrodes of the front quadrupole mass filter 231 so that the precursor ion which has been set as the reference MRM transition candidate among the various ions sent into the front quadrupole mass filter 231 is allowed to pass through the front quadrupole mass filter 231. Meanwhile, CID gas is supplied to the collision cell 232, and a voltage based on the CE value in the compound information is applied to the same cell. Additionally, a predetermined form of voltage (composed of a radio-frequency voltage and a direct-current voltage superposed on each other) is applied to the rear quadrupole mass filter 234 so that only the product ion which has been set as the reference MRM transition candidate is selected from the various product ions produced from the precursor ion fragmented in the collision cell 232. The ion detector 235 detects the ions which have passed through the rear quadrupole mass filter 234, and sends pulse signals whose number corresponds to the number of those ions to the data processing unit 24 as detection signals. The parameters relating to the MS/MS analysis conditions, such as the mass-resolving power of the front quadrupole mass filter (Q1) 231 and that of the rear quadrupole mass filter (Q3), are set at normal values (e.g. initial values).

Based on the detection signals from the ion detector 235, the mass chromatogram acquirer 243 creates a mass chromatogram for the reference MRM transition candidate and saves it in the storage section 241. It also displays the mass chromatogram on the screen of the display unit 7.

Next, the shape similarity calculator 244 extracts the peak at a position corresponding to the retention time (tb) of compound "B" in the mass chromatogram, and calculates the shape similarity between the extracted peak and the model-peak shape (Step S23). The method for calculating the shape similarity is as already described.

If the calculated shape similarity is equal to or higher than a predetermined value ("YES" in Step S24), the ion-combination designator 246 designates the currently selected reference MRM transition candidate as the MRM transition (Step S29) and creates an MRM method including the MS/MS analysis conditions (such as the normal setting of the resolving power of the quadrupole mass filters) under which the mass chromatogram was acquired (Step S30).

If the calculated shape similarity is lower than the predetermined value ("NO" in Step S24), the MS/MS analysis condition modifier 245 changes the MS/MS analysis conditions. In the present embodiment, the MS/MS analysis conditions are modified by increasing each of the mass-resolving powers of the front quadrupole mass filter (Q1) 231 and the rear front quadrupole mass filter (Q3) to one higher level. It is also possible to increase the mass-resolving power of only one of the two filters Q1 and Q3 instead of increasing the mass-resolving power in both of them.

After the MS/MS analysis conditions are modified, the mass chromatogram for the reference MRM transition candidate is once more acquired under the modified conditions (Step S26), and the shape similarity between the peak on the mass chromatogram and the model peak is calculated (Step S27).

If the shape similarity calculated after the modification to the MS/MS analysis conditions is equal to or higher than the predetermined value ("YES" in Step S28), the ion-combination designator 246 designates the currently selected reference MRM transition candidate as the MRM transition (Step S29) and creates an MRM method including the modified MS/MS analysis conditions, such as the increased resolving powers of the quadrupole mass filters (Step S30).

If the calculated shape similarity is lower than the predetermined value ("NO" in Step S28), the ion-candidate combination setter 242 sets another reference MRM transition candidate. After that, the processes of Step S22 and subsequent steps are performed to select the reference MRM transition (Step S29) and create an MRM method (Step S30).

Fourth Embodiment

The description in the third embodiment is premised on that the compound information has been prepared beforehand. However, for some kinds of target compounds, it is possible that no compound information is present.

The mass spectrometry method and system as the fourth embodiment are used in such a case in order to select an MRM transition candidate and determine the value of the collision energy (CE) corresponding to that transition candidate.

To clarify the feature of the fourth embodiment, a conventionally used method is initially described.

Figure 11:
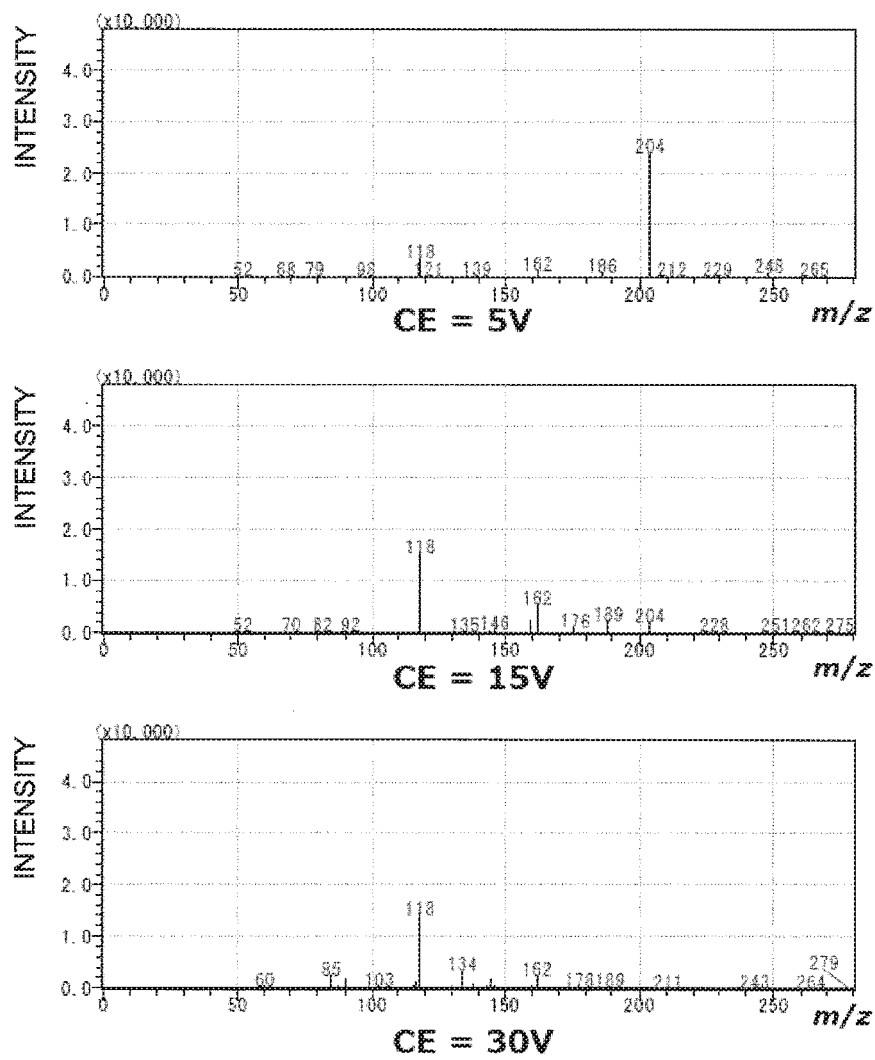
FIG. 11 is an example of the mass spectra acquired by a product ion scan measurement.

An analysis operator sets one of the ions generated from a target compound as the precursor ion and conducts a product-ion scan measurement under a plurality of conditions with different amounts of collision energy to obtain product-ion spectra. For example, FIG. 11 shows product-ion spectra acquired under three conditions with the CE values set at 5 V, 15 V and 30 V, respectively. An example of the precursor ion is an ion corresponding to a peak having a high intensity in a mass spectrum acquired by a mass spectrometry of the target compound or an ion produced by the protonation of the target compound. From the obtained product-ion spectra, a product-ion peak having a high intensity is selected. Ultimately, the product ion corresponding to that peak is identified and the value of the collision energy is determined (see Patent Literature 3 or 4). In the example of FIG. 11, the mass-to-charge ratio of the product ion is m/z=204, and the CE value is 5 V.

This method has two problems.

Figure 12:
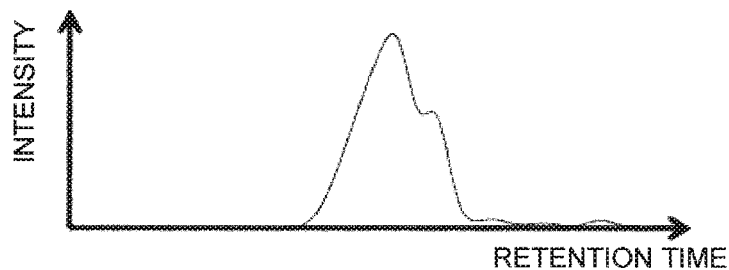
FIG. 12 is an example of the peak shape in the mass chromatogram acquired for an MRM transition selected by a conventional method.

The first problem is that a peak of a foreign component may appear in an overlapped form in a mass spectrum acquired by an MRM measurement using the selected MRM transition. For example, an ion which originates from the mobile phase used in the liquid chromatograph may appear as a foreign component, in which case the chromatogram peak will have a shape as shown in FIG. 12. Using such an MRM transition in the measurement of a real sample will lead to an incorrect determination of the quantity of the target compound including the simultaneously eluted foreign component, or to an incorrect conclusion that the target compound is contained even when no such compound is actually contained.

Figure 13:
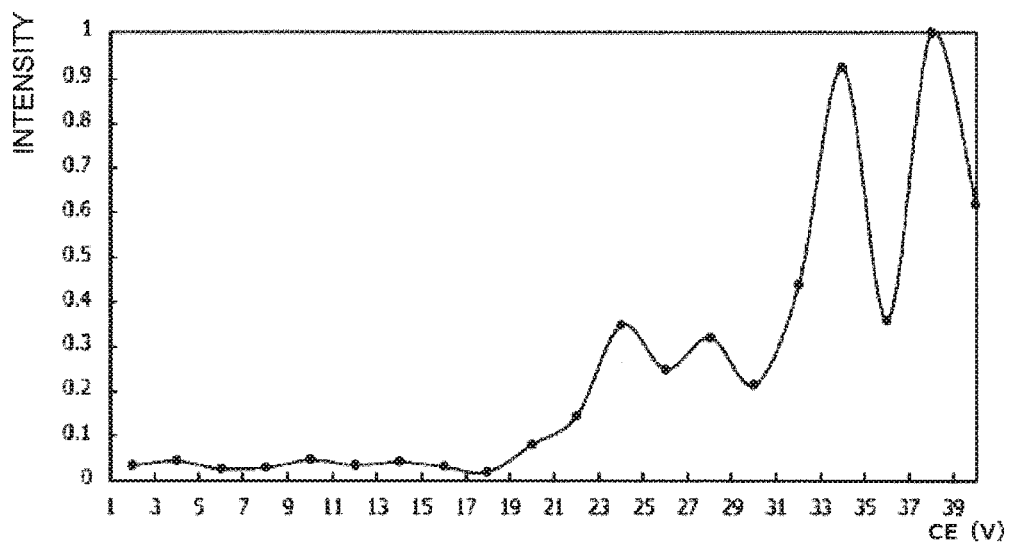
FIG. 13 is a graph illustrating the change in the product-ion intensity with respect to the CE value.

The second problem is that a discrepancy between the CE value used in the MRM measurement and the determined CE value may possibly cause a significant decrease in the generation efficiency of the product ion. As can be seen in FIG. 11, using a different CE value changes the kinds and amounts of product ions to be generated. For some kinds of product ions, a slight difference in the CE value may cause a significant change in the generation efficiency (i.e. the peak intensity of the mass chromatogram observed in the MRM measurement), as shown in FIG. 13. If an MRM transition including such a product ion is used, the peak intensity obtained in the MRM measurement of a real sample may become insufficient, which may lead to an incorrect conclusion that the target compound is not contained even when the compound is actually contained.

Figure 14:
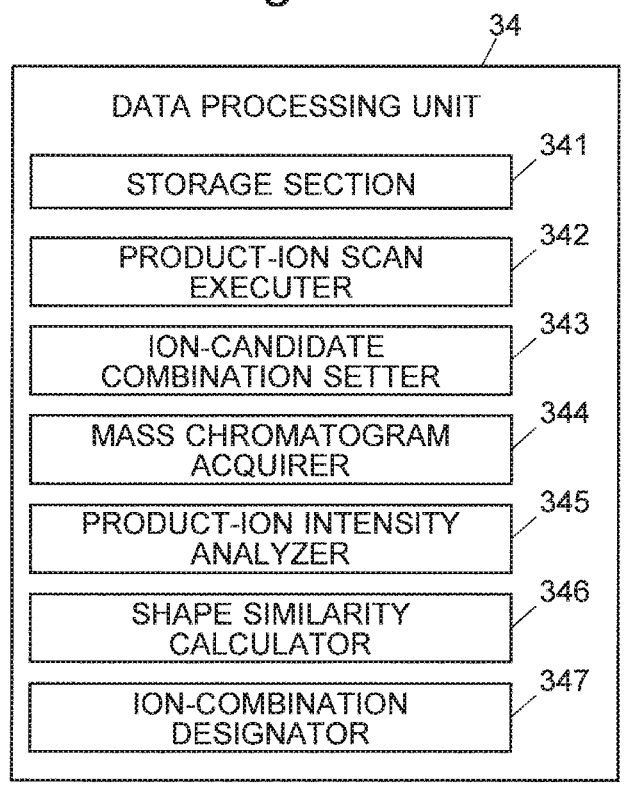
FIG. 14 is a diagram illustrating the configuration of the data processing unit of the mass spectrometer in the fourth embodiment.

The mass spectrometry method and mass spectrometer in the fourth embodiment are configured to solve such problems in selecting an appropriate MRM transition candidate and the CE value corresponding to the candidate. The configuration of each section of the liquid chromatograph mass spectrometer in the fourth embodiment is the same as in the first embodiment except for the data processing unit 34. Accordingly, only the configuration of the data processing unit 34 is shown in FIG. 14.

The data processing unit 34 has a storage section 341 as well as a product-ion scan executer 342, ion-candidate combination setter 343, mass chromatogram acquirer 344, product-ion intensity analyzer 345, shape similarity calculator 346 and ion-combination designator 347 as its functional blocks. The storage section 341 holds the model-peak function information and the retention time (or retention index) for the analyte compound described in the first embodiment, as well as information concerning a model function which is different from the model-peak function.

Figure 15:
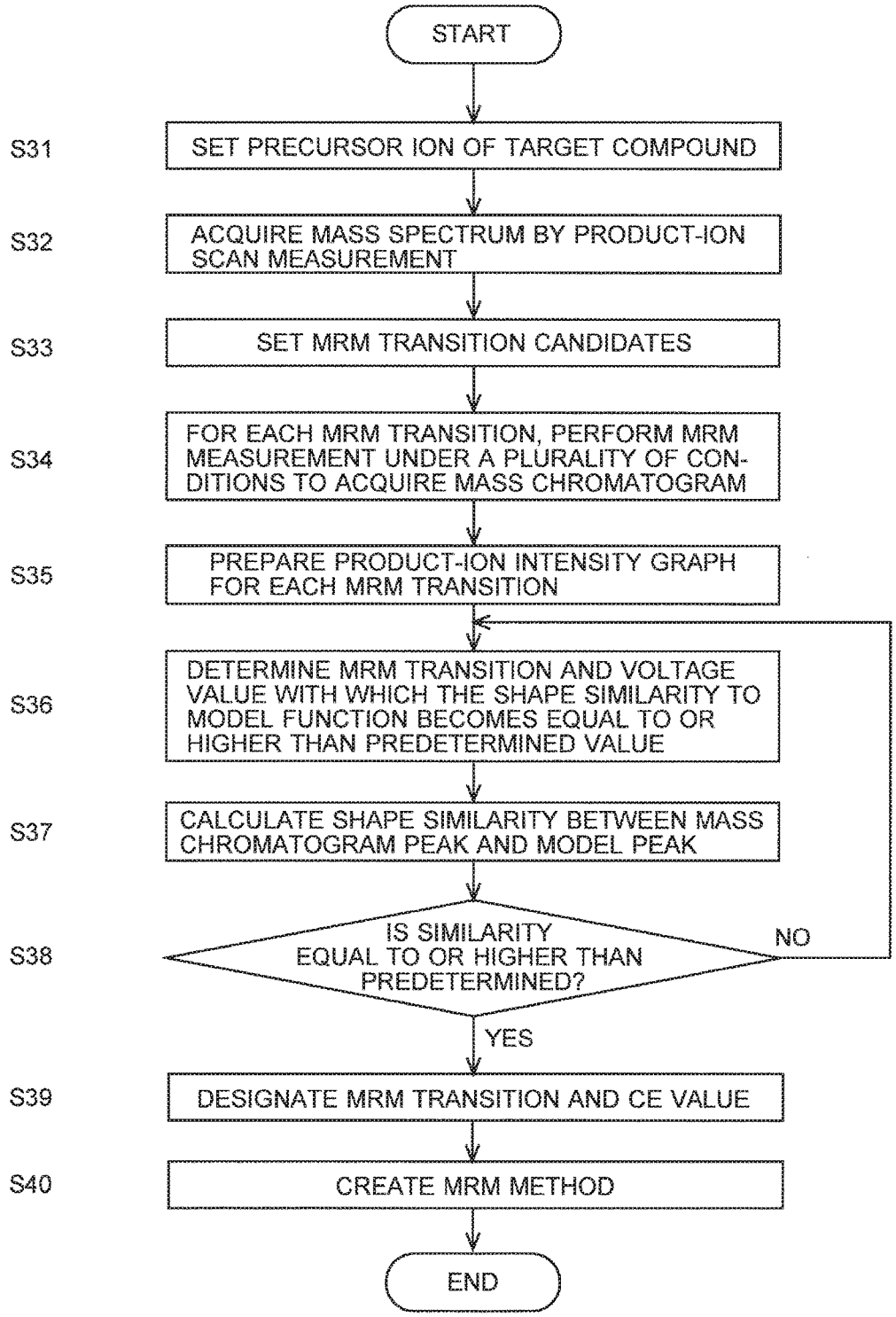
FIG. 15 is a flowchart in the mass spectrometry method in the fourth embodiment.

The mass spectrometry method in the fourth embodiment is described with reference to the flowchart of FIG. 15.

After the precursor ion of the target compound is set by an analysis operator (Step S31), the product-ion scan executer 342 performs a product-ion scan measurement for the precursor ion and acquires a mass spectrum (Step S32). At this point, the CE value is set at a normal value (e.g. the initial value for the device). If a plurality of precursor ions have been set by the analysis operator, the product-ion scan is performed for each precursor ion to acquire the mass spectrum.

Subsequently, the ion-candidate combination setter 343 designates, as the product-ion candidates, the ions corresponding to the peaks having intensities equal to or higher than a predetermined value on the mass spectrum, and sets those ions in combination with the precursor ion set by the user as MRM transition candidates (Step S33).

After the MRM transition candidates are set, the mass chromatogram acquirer 344 acquires a mass chromatogram for each of the set MRM transitions under a plurality of conditions with different CE values (Step S34). The product-ion intensity analyzer 345 determines the intensity (or area) of the peak on each mass chromatogram and creates a product-ion intensity graph showing a plot of the peak intensity with respect to the CE value (Step S35). FIG. 16 shows an example of the product-ion intensity graph created by the product-ion intensity analyzer 345.

The shape similarity calculator 346 calculates the shape similarity between the product-ion intensity graph and the model function, and selects a product ion which shows only a small amount of change in its intensity with a change in the CE value (Step S36). In the present embodiment, a function which shows no change in the intensity with a change in the CE value (i.e. y=k, where k is a constant) is used as the model function. The shape similarity calculator 346 calculates the shape similarity between this model function and the product-ion intensity graph, locates a range in which the shape similarity is high, and selects the MRM transition as well as the voltage value corresponding to that range. In the present embodiment, since the aforementioned function is used, a high level of shape similarity is achieved as shown in graph (ii) of FIG. 16, i.e. when the mass-to-charge ratio of the product ion is m/z=B and the CE value is within a range from 20 to 28 V (where the amount of change in the product-ion intensity with a change in the CE value is small).

After selecting the combination of the MRM transition and the voltage value, the shape similarity calculator 346 calculates the shape similarity between the peak on the mass chromatogram acquired for that combination and the model-peak function (Step S37), and subsequently determines whether or not the calculated similarity is equal to or higher than a predetermined value (Step S38). The method for calculating the shape similarity of the peak on the mass chromatogram is as described in the first embodiment.

The ion-combination designator 347 selects each MRM transition candidate which satisfies the condition that the shape similarity between the peak on the mass chromatogram and the model-peak function calculated by the shape similarity calculator 346 is equal to or higher than the predetermined value, and determines the CE value corresponding to that candidate (Step S39), and creates an MRM method including them (Step S40). In this manner, the compound information for the target compound is prepared and saved in the storage section 341.

In the previous description, the determination on the similarity of the product-ion intensity graph is followed by the determination on the shape similarity of the peak on the mass chromatograph. It is possible to reverse the order of these determinations. In the case of using a standard sample to create an MRM method, a flow injection analysis or similar analysis may be performed without using the column 113, because it is unnecessary to separate the components.

Although a liquid chromatograph mass spectrometer is used as one example in the previous embodiments, a gas chromatograph mass spectrometer may also be similarly used. Furthermore, as opposed to the previously described examples in which there is only one compound "A" or "B" to be analyzed, if there are a plurality of analyte compounds, the previously described steps can be performed for each of those analyte compounds.

In the previous embodiments, a peak represented by a specific function is used as the model peak. Alternatively, a peak obtained in the actual measurement of a standard sample may also be used.

The configuration in the first embodiment may be modified so that the determination on the shape similarity of the mass-chromatogram peak is initiated from the reference-ion candidate which is given the highest priority. The configuration in the third embodiment may be modified so as to collectively acquire mass chromatograms for all reference MRM transition candidates and subsequently select reference MRM transitions taking into account the shape similarities and intensities of the peaks.

In the example described in the second embodiment, the combination of the target ion and the qualifier ion is selected based on the peak intensity value of the mass chromatogram. In a similar manner, the combination of the target MRM transition and the qualifier MRM transition can also be selected based on the peak intensity value of the mass chromatogram acquired by an MRM measurement.

In any of the previous embodiments, the data processing unit is configured to actively select the reference ion. The system may also be configured so that the analysis operator is allowed to manually select the reference ion, while the data processing unit displays an alert message and prompts the analysis operator to reselect the reference ion only when the shape similarity (or peak intensity ratio) of the reference ion selected by the analysis operator is equal to or lower than a predetermined value.

REFERENCE SIGNS LIST

1 . . . Liquid Chromatograph Unit
110 . . . Mobile Phase Container
111 . . . Pump
112 . . . Injector
113 . . . Column
2 . . . Mass Spectrometer
20 . . . Ionization Chamber
201 . . . Electrospray Ionization (ESI) Probe
202 . . . Heated Capillary
21 . . . First Intermediate Vacuum Chamber
211 . . . Ion Guide
212 . . . Skimmer
22 . . . Second Intermediate Vacuum Chamber
221 . . . Ion Guide 23 . . . Analysis Chamber
231 . . . Front Quadrupole Mass Filter
232 . . . Collision Cell
233 . . . Multipole Ion Guide
234 . . . Rear Quadrupole Mass Filter
235 . . . Ion Detector
3 . . . Power Source
4, 14, 24, 34 . . . Data Processing Unit
41, 141, 241, 341 . . . Storage Section
42 . . . Reference-Ion Candidate Setter
43, 143, 243, 344 . . . Mass Chromatogram Acquirer
44, 244, 346 . . . Shape Similarity Calculator
45 . . . Reference-Ion Designator
142, 242, 343 . . . Ion-Candidate Combination Setter
144 . . . Peak Ratio Calculator
145, 246, 347 . . . Ion-Combination Designator
245 . . . MS/MS Analysis Condition Modifier
342 . . . Product-Ion Scan Executer
345 . . . Product-Ion Intensity Analyzer

The invention claimed is:

1. A mass spectrometry method for performing a qualitative and/or quantitative determination of an analyte compound contained in a sample, using a mass chromatogram acquired for one or a plurality of ions selected as a reference ion from ions produced from the analyte compound, the method comprising steps of:
  a) setting a plurality of reference-ion candidates;
  b) acquiring a mass chromatogram of the sample for each of the set reference-ion candidates by operating a chromatograph to separate compounds and operating a mass spectrometer to measure mass-to-charge ratios of ionized compounds;
  c) calculating a shape similarity between a peak appearing at a predetermined position on the mass chromatogram and a model peak represented by a previously defined function; and
  d) designating, as the reference ion, a reference-ion candidate corresponding to a peak having the shape similarity equal to or higher than a predetermined value.

2. The mass spectrometry method according to claim 1, wherein the reference ion is a target ion and/or a qualifier ion.

3. The mass spectrometry method according to claim 1, wherein the reference ion is a combination of a precursor ion and a product ion.

4. The mass spectrometry method according to claim 1, wherein a reference-ion candidate having an intensity or area value of the peak on the mass chromatogram equal to or higher than a predetermined value is designated as the reference ion.

5. The mass spectrometry method according to claim 1, wherein the steps of acquiring the mass chromatogram and calculating the shape similarity are performed in descending order of priority of the reference-ion candidates, where these steps are similarly repeated for the reference-ion candidate ranked next in the order of priority if the shape similarity is equal to or lower than the predetermined value.

6. The mass spectrometry method according to claim 1, wherein, if the shape similarity is equal to or lower than the predetermined value, the steps of acquiring a mass chromatogram and calculating the shape similarity for the mass chromatogram are once more performed after modifying an analysis condition.

7. The mass spectrometry method according to claim 6, wherein the analysis condition to be changed relates to a resolving power of a mass separator section.

8. A mass spectrometry method for performing a qualitative and/or quantitative determination of an analyte compound contained in a sample, using a mass chromatogram acquired for one or a plurality of reference ions, where each reference ion is a combination of a precursor ion and a product ion selected from ions produced from the analyte compound, the method comprising steps of:
  a) setting a plurality of reference-ion candidates;
  b) acquiring a mass chromatogram for each of the plurality of reference ion candidates by operating a chromatograph to separate compounds, and operating a mass spectrometer to measure mass-to-charge ratios of ionized compounds at different collision energy voltage values applied to a collision cell;
  c) creating, for each of the set reference-ion candidates, a graph showing a relationship between an amount of product ions generated by fragmenting the precursor ion in the collision cell and a magnitude of a voltage applied to the collision cell; and
  d) calculating a shape similarity between the graph and a preset model function, and selecting a reference-ion candidate and a voltage value giving the shape similarity equal to or higher than a predetermined value.

9. A mass spectrometry analysis device for performing a qualitative and/or quantitative determination of an analyte compound contained in a sample, using a mass chromatogram acquired for one or a plurality of ions selected as a reference ion from ions produced from the analyte compound, the mass spectrometry analysis device comprising:
  a) a chromatograph configured to separate compounds;
  b) a mass spectrometer configured to measure mass-to-charge ratios of ionized compounds;
  c) a storage section for holding model-peak information concerning a peak shape of a model peak represented by a previously defined function;
  d) a reference-ion candidate setter for setting a plurality of reference-ion candidates;
  e) a mass chromatogram acquirer for acquiring a mass chromatogram of the sample for each of the set reference-ion candidates by operating the chromatograph and the mass spectrometer;
  f) a shape similarity calculator for calculating a shape similarity between a peak appearing at a predetermined position on the mass chromatogram and the model peak based on the model-peak information; and
  g) a reference-ion designator for designating, as the reference ion, a reference-ion candidate corresponding to a peak having the shape similarity equal to or higher than a predetermined value.

10. The mass spectrometry method according to claim 1, wherein:
  the reference ion is a combination of a target ion and a qualifier ion, while the reference-ion candidates are combinations of target-ion candidates and qualifier-ion candidates; and
  the method further comprises steps of:
    calculating a value of an area ratio or intensity ratio between a peak appearing at a predetermined position on the mass chromatogram of the target-ion candidate and a peak appearing at the predetermined position on the mass chromatogram of the qualifier-ion candidate; and
    designating, as a combination of the target ion and the qualifier ion, a combination of the target-ion candidate and the qualifier-ion candidate if the value of the area ratio or intensity ratio calculated for this combination is within a preset range.

11. The mass spectrometer according to claim 9, wherein:
the reference ion is a combination of a target ion and a qualifier ion, while the reference-ion candidates are combinations of target-ion candidates and qualifier-ion candidates;
the storage section further holds ion-combination information concerning an area ratio and/or intensity ratio between peaks on mass chromatograms for each of one or a plurality of combinations of target-ion candidates and qualifier-ion candidates corresponding to the analyte compound;
the mass spectrometer further comprises a peak ratio calculator for calculating a value of the area ratio or intensity ratio between a peak appearing at a predetermined position on the mass chromatogram of the target-ion candidate and a peak appearing at the predetermined position on the mass chromatogram of the qualifier-ion candidate; and
the reference-ion designator designates, as the reference ion, a combination selected from the combinations of the target-ion candidates and the qualifier-ion candidates, the selected combination having a value of the area ratio or intensity ratio within a preset range based on the ion-combination information.

12. A mass spectrometry analysis device for performing a qualitative and/or quantitative determination of an analyte compound contained in a sample, using a mass chromatogram acquired for one or a plurality of reference ions, where each reference ion is a combination of a precursor ion and a product ion selected from ions produced from the analyte compound, the mass spectrometry analysis device comprising:
a) a chromatograph configured to separate compounds;
b) a mass spectrometer configured to measure mass-to-charge ratios of ionized compounds;
c) an ion candidate setter configured to set a plurality of reference-ion candidates;
d) a mass chromatogram acquirer configured to acquire a mass chromatogram for each of the plurality of reference ion candidates by operating the chromatograph to separate compounds, and operating the mass spectrometer to measure mass-to-charge ratios of ionized compounds at different collision energy voltage values applied to a collision cell;
e) a product ion intensity analyzer configured to create, for each of the set reference-ion candidates, a graph showing a relationship between an amount of product ions generated by fragmenting the precursor ion in the collision cell and a magnitude of a voltage applied to the collision cell; and
f) a shape similarity calculator configured to calculate a shape similarity between the graph and a preset model function, and selecting a reference-ion candidate and a voltage value giving the shape similarity equal to or higher than a predetermined value.

* * * * *